United States Patent
Chen et al.

(10) Patent No.: US 11,970,507 B2
(45) Date of Patent: *Apr. 30, 2024

(54) METHOD FOR PREPARING 2-ARYLMALONIC ACID DERIVATIVE AND INTERMEDIATE, AND USE THEREOF

(71) Applicant: ORIENTAL(LUZHOU) AGROCHEMICALS CO., LTD., Sichuan (CN)

(72) Inventors: Bangchi Chen, Sichuan (CN); Yinwei Sun, Sichuan (CN); Zhongyuan Wang, Sichuan (CN); Tao Jin, Sichuan (CN)

(73) Assignee: ORIENTAL (LUZHOU) AGROCHEMICALS CO., LTD., Luzhou (CN)

( * ) Notice: Subject to any disclaimer, the term of this patent is extended or adjusted under 35 U.S.C. 154(b) by 120 days.

This patent is subject to a terminal disclaimer.

(21) Appl. No.: 17/489,630

(22) Filed: Sep. 29, 2021

(65) Prior Publication Data
US 2022/0064184 A1    Mar. 3, 2022

Related U.S. Application Data

(63) Continuation of application No. PCT/CN2019/080827, filed on Apr. 1, 2019.

(51) Int. Cl.
*C07D 498/04* (2006.01)
*C07C 253/30* (2006.01)
*C07C 255/41* (2006.01)

(52) U.S. Cl.
CPC .......... *C07D 498/04* (2013.01); *C07C 253/30* (2013.01); *C07C 255/41* (2013.01); *C07C 2601/16* (2017.05)

(58) Field of Classification Search
CPC .................................................. C07D 498/04
See application file for complete search history.

(56) References Cited

FOREIGN PATENT DOCUMENTS

| | | | |
|---|---|---|---|
| CN | 102617450 B | 8/2014 | |
| CN | 106928253 A | 7/2017 | |
| CN | 108264463 A | 7/2018 | |
| CN | 108264469 A | 7/2018 | |
| CN | 108264517 A | 7/2018 | |
| CN | 108689874 A | 10/2018 | |
| WO | 0078712 A1 | 12/2000 | |
| WO | 0078881 A2 | 12/2000 | |
| WO | WO 2000078712 * | 12/2000 | ........... C07C 255/33 |
| WO | 2004050607 A1 | 6/2004 | |
| WO | 2018120094 A1 | 7/2018 | |
| WO | 2018184196 A1 | 10/2018 | |

OTHER PUBLICATIONS

Long, ACS Catalysis (2022), 12(8), 4688-4695.*
Zav'yalov, Izvestiya Akademii Nauk SSSR, Seriya Khimicheskaya (1980), (11), 2575-8.*
Benassi, R.,et al.Ground-state molecular stabilization of substituted ethylenes. A theoretical mo ab-initio thermochemical study. Journal of Molecular Structure: THEOCHEM, 572, (Sep. 17, 2001) 169-183.
Zi, W., & Toste, F. D. Gold(I)-Catalyzed Enantioselective Desymmetrization of 1,3-Diols through Intramolecular Hydroalkoxylation of Allenes. Angewandte Chemie International Edition, 54(48), 14447-14451.
J. Chem. Soc., Chem. Commun., 1984, 932.

* cited by examiner

*Primary Examiner* — Nizal S Chandrakumar

(57) ABSTRACT

Disclosed herein is a method for preparing a 2-arylmalonic acid derivative. In this method, a cyclohexadiene compound is used as a raw material, and sequentially undergoes an isomerization reaction, a halogenation reaction in the presence of a halogenating agent and a dehydrohalogenation-aromatization reaction to obtain a 2-arylmalonic acid derivative (3). An intermediate for preparing the 2-arylmalonic acid derivative (3) and use of the intermediate are also disclosed.

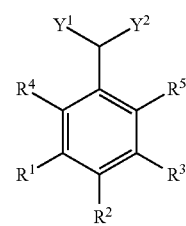

3

4 Claims, No Drawings

METHOD FOR PREPARING 2-ARYLMALONIC ACID DERIVATIVE AND INTERMEDIATE, AND USE THEREOF

CROSS-REFERENCE TO RELATED APPLICATIONS

This application is a continuation of International Patent Application No. PCT/CN2019/080827, filed on Apr. 1, 2019. The content of the aforementioned applications, including any intervening amendments thereto, is incorporated herein by reference in its entirety.

TECHNICAL FIELD

This application relates to organic synthesis, and more particularly to a method for preparing a 2-arylmalonic acid derivative, and an intermediate, and use thereof.

BACKGROUND

2-Arylmalonic acid derivatives, as an important class of organic compounds, are widely used in the preparation of materials, medicines and pesticides. For example, 2-phenylmalonate is a significant raw material for the preparation of polymer stabilizers (CN 102617450B); and 2-(2,6-diethyl-4-methylphenyl) malonate diester and 2-(2,6-diethyl-4-methylphenyl) malononitrile are crucial intermediates for preparing highly-effective herbicide Pinoxaden (WO 00/78881).

Currently, the reported strategies for preparing the 2-arylmalonic acid derivatives may be divided into three categories according to the construction of C—C bond.

The first type of strategy is characterized by constructing a skeleton of a target compound through the C—C coupling of a halogenated aromatic hydrocarbon and a malonic acid derivative under the action of a catalyst (Journal of the Chemical Society, Chemical Communications (1984), (14), 932-3, WO 00/78712 and WO 2004/050607). This method usually requires an expensive organometallic catalyst, and the catalyst is difficult to recycle, leading to a high cost. In addition, active halogenated aromatic hydrocarbons such as brominated or iodized aromatic hydrocarbons are generally required as raw materials. However, the halogenated aromatic hydrocarbons, especially those with different substituents at specific positions, are difficult to synthesize, and are usually prepared from the corresponding aniline by diazo-halogenation reaction. The diazo-halogenation reaction not only involves the generation of a large quantity of wastes, but also carries problems of safety concerns and halogen corrosion.

With respect to the second type of strategy, a phenylacetic acid derivative is used as a raw material and undergoes a condensation reaction with a dialkyl carbonate in the presence of a strong base (i.e., sodium hydride) to construct the skeleton of the target compound (Zi, W. and Toste, F. D. Gold(I)-Catalyzed Enantioselective Desymmetrization of 1,3-Diols through Intramolecular Hydroalkoxylation of Allenes. Angew. Chem. Int. Ed., (2015), 54(48), 14447-14451). However, the phenylacetic acid derivatives, especially the multi-substituted phenylacetic acid derivatives, are difficult to prepare. In addition, the strong base such as sodium hydride (needing anhydrous and oxygen-free operation) and the hydrogen produced by the reaction will cause major safety hazards. Therefore, this method is not suitable for industrial production.

The third type of strategy is to use a 2-(cyclohexenylidene)malonic acid derivative as a raw material to obtain the target product through dehydrogenation reaction at 180-200° C. in the presence of a metal catalyst (generally a noble metal, such as palladium) (WO 2018/120094). This method has high cost and high reaction temperature, and thus is not conducive to the industrial production.

SUMMARY

Aiming at the shortcomings of the prior art, the present disclosure provides a method for preparing a 2-arylmalonic acid derivative, which is safe and economical, and suitable for industrial production.

A method for preparing a 2-arylmalonic acid derivative of formula (3), comprising:

(1) subjecting a compound (1) to an isomerization reaction to obtain an intermediate (2), as shown in the following reaction scheme:

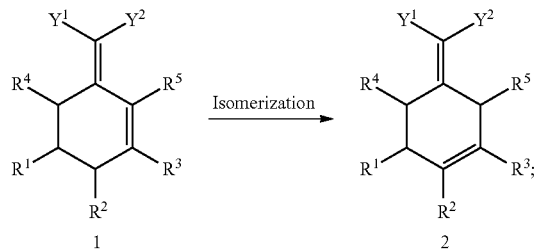

(2) subjecting the intermediate (2) to a halogenation reaction in the presence of a halogenating agent and a dehydrohalogenation-aromatization reaction to obtain the 2-arylmalonic acid derivative (3), as shown in the following reaction scheme:

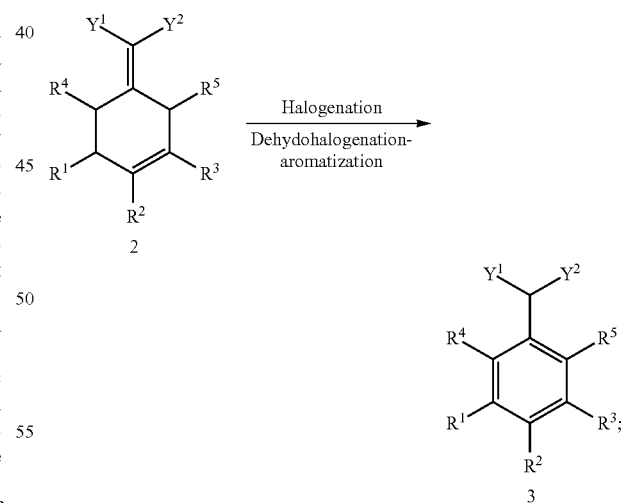

wherein $R^1$, $R^2$, $R^3$, $R^4$ and $R^5$ each are independently hydrogen, a $C_1$-$C_{10}$ alkyl group, a $C_6$-$C_{12}$ aryl group or a heteroaryl group containing one or two atoms selected from nitrogen, oxygen and sulfur;

$Y^1$ and $Y^2$ are each independently cyano or —$COR^6$ where $R^6$ is hydrogen, a $C_1$-$C_{10}$ alkyl group, a $C_1$-$C_{10}$ alkoxy group, a $C_6$-$C_{12}$ aryloxy group, amino, a $C_1$-$C_{10}$ alkylamino group, a $C_6$-$C_{12}$ arylamino group, a di-($C_1$-

$C_{10}$ alkyl)-amino group, a ($C_1$-$C_{10}$ alkyl)-($C_6$-$C_{12}$ aryl)-amino group, a di-($C_6$-$C_{12}$ aryl) amino group, a $C_6$-$C_{12}$ aryl group or a heteroaryl group containing one or two atoms selected from nitrogen, oxygen and sulfur.

In some embodiments, $R^1$, $R^2$, $R^3$, $R^4$ and $R^5$ are each independently hydrogen, a $C_1$-$C_4$ alkyl group or a $C_6$-$C_{12}$ aryl.

In some embodiments, $Y^1$ and $Y^2$ are each independently cyano, —COOMe, —COOEt or —CONH$_2$.

In some embodiments, in step (1), the isomerization reaction is carried out in the presence of a base; and the base is selected from the group consisting of an alkali metal hydroxide, an alkali metal alcoholate, an alkaline earth metal hydroxide, an alkaline earth metal alcoholate and a combination thereof, preferably sodium hydroxide or sodium methoxide;

a molar ratio of the base to the compound (1) is (0.8-2.4):1, preferably (1.0-1.2):1; and in step (2), the halogenating reagent is selected from the group consisting of an elemental halogen (such as chlorine gas and liquid bromine), a hypohalous acid (such as hypochlorous acid and hypobromous acid), a sulfuryl halide (such as a sulfuryl chloride), a thionyl halide (such as thionyl chloride) and a combination thereof, preferably chlorine gas, sulfuryl chloride or liquid bromine.

In some embodiments, in step (2), the dehydrohalogenation-aromatization reaction is carried out under an action of a catalyst; and the catalyst is selected from the group consisting of an alkali metal halide, an alkaline earth metal halide and a combination thereof, preferably lithium chloride or sodium chloride.

In some embodiments, a molar ratio of the catalyst to the intermediate (2) is (0.005-2.4):1, preferably (0.02-0.1):1.

In some embodiments, in step (2), the dehydrohalogenation-aromatization reaction is carried out at 0-150° C., preferably 110-150° C.

In some embodiments, the above preparation method of the 2-arylmalonic acid derivative (3) is carried out in a one-pot manner.

The 2-arylmalonic acid derivative (3) prepared by the method mentioned above, for example, 2-(2,6-diethyl-4-methylphenyl)malononitrile, can be used to prepare 8-(2,6-diethyl-4-methylphenyl)-7-oxo-1,2,4,5-tetrahydro-7H-pyrazole[1,2-d][1,4,5]oxadiazepine-9-pyrivalate (Pinoxaden) through further transformation and reaction.

The beneficial effects of the present disclosure are described as follows.

(1) The reaction does not require expensive metal catalysts.
(2) The reaction avoids the use of strong bases with potential safety hazards.
(3) The reactions are safe, the conditions are mild, yields are high and cost is low, making it suitable for the industrial production.

DETAILED DESCRIPTION OF EMBODIMENTS

The technical solutions of the present disclosure will be further described below with reference to the embodiments, and the embodiments are not intended to limit the scope of the present disclosure.

The raw material 1 is prepared by a method known in the prior art (for example, WO2018/120094).

Example 1 Preparation of
2-(2,6-diethyl-4-methyl-3-ene-1-cyclohexylidene) malononitrile To a 250 mL three-necked flask equipped with a magnetic stirrer and a thermometer were sequentially added 85.0 g of methanol and 42.9 g of 2-(2,6-diethyl-4-methyl-2-ene-1-cyclohexylidene) malononitrile. The reaction mixture was stirred and heated to 50° C. 10.8 g of sodium methoxide was added. The reaction was stirred for 5 min. The reaction mixture was cooled, acidificated, extracted, concentrated and separated to give 39.0 g of 2-(2,6-diethyl-4-methyl-3-ene-1-cyclohexylidene) malononitrile (91% yield).

$^1$H NMR (CDCl$_3$, 500 MHz, TMS): δ 41 (m, 1H), 3.23 (m, 1H), 3.12 (q, J=7.5 Hz, 1H), 2.40-2.35 (m, 1H), 2.15 (d, J=17.5 Hz, 1H), 1.73 (d, J=1.5 Hz, 3H), 1.68-1.59 (m, 4H), 1.13 (t, J=7.5 Hz, 3H), 0.95 (t, J=7.6 Hz, 3H).

$^{13}$C NMR (CDCl$_3$, 125 MHz): δ 189.5, 131.7, 119.0, 111.9, 111.7, 84.8, 44.0, 43.0, 35.9, 30.5, 27.4, 23.3, 12.8, 12.2.

Example 2 Preparation of
2-(2,6-diethyl-4-methyl-3-ene-1-cyclohexylidene) malononitrile To a 250 mL three-necked flask equipped with a magnetic stirrer and a thermometer were sequentially added 85.0 g of tetrahydrofuran and 42.9 g of 2-(2,6-diethyl-4-methyl-2-ene-1-cyclohexylidene) malononitrile. The reaction mixture was stirred and heated to 50° C., and 11.22 g of potassium hydroxide was added. The reaction was stirred for 30 min. The reaction mixture was cooled, acidificated, extracted, concentrated and separated to give 36.9 g of 2-(2,6-diethyl-4-methyl-3-ene-1-cyclohexylidene) malononitrile (86% yield).

Example 3 Preparation of
2-(2,6-diethyl-4-methylphenyl) malononitrile

To a 250 mL three-necked flask equipped with a magnetic stirrer, a thermometer and a reflux condenser were sequentially added 125 g of chlorobenzene and 53.5 g of 2-(2,6-diethyl-4-methyl-3-ene-1-cyclohexylidene) malononitrile prepared in Example 1. The reaction mixture was stirred, cooled to 0° C., and introduced with chlorine gas until the reaction was complete. The reaction mixture was then concentrated, 200 mL of N,N-dimethylformamide and 0.42 g of LiCl were sequentially added, and refluxed until the reaction was complete. After that, the reaction mixture was cooled, extracted, washed, concentrated and separated to give 47.8 g of 2-(2,6-diethyl-4-methylphenyl) malononitrile (90% yield).

Example 4 Preparation of
2-(2,6-diethyl-4-methylphenyl) malononitrile

To a 500 mL three-necked flask equipped with a magnetic stirrer and a thermometer were sequentially added 125.0 g of N,N-dimethylformamide and 64.4 g of 2-(2,6-diethyl-4-methyl-3-ene-1-cyclohexylidene) malononitrile prepared in Example 1. The reaction mixture was stirred, cooled to 0° C., and introduced with chlorine gas until the reaction was complete. The reaction mixture was then concentrated, 300 mL of N-methylpyrrolidone was added and heated to 130° C. until the reaction was complete. The reaction mixture was cooled to room temperature, and extracted, washed, concentrated and separated to give 51.0 g of 2-(2,6-diethyl-4-methylphenyl) malononitrile (80% yield).

Example 5 Preparation of 2-(2,6-diethyl-4-methylphenyl) malononitrile

To a 250 mL three-necked flask equipped with a magnetic stirrer, a thermometer and a reflux condenser were sequentially added 85.0 g of acetic acid and 21.5 g of 2-(2,6-diethyl-4-methyl-3-ene-1-cyclohexylidene) malononitrile prepared in Example 1. The reaction mixture was stirred, heated to 45° C., 60 g of an acetic acid solution containing 17.6 g of liquid bromine were added and reacted at 45° C. for 2 h. The reaction solution was then concentrated, 100 mL of N,N-dimethylformamide and 0.95 g of LiBr sequentially were added and refluxed until the reaction was complete. After that, the reaction mixture was cooled, extracted, washed, concentrated and separated to give 10.6 g of 2-(2,6-diethyl-4-methylphenyl) malononitrile (50% yield).

Example 6 Preparation of 2-(2,6-diethyl-4-methylphenyl) malononitrile

To a 500 mL three-necked flask equipped with a magnetic stirrer and a thermometer were sequentially added 170.0 g of acetic acid and 42.9 g of 2-(2,6-diethyl-4-methyl-3-ene-1-cyclohexylidene) malononitrile prepared in Example 1. The reaction mixture was stirred, heated to 45° C., 29.8 g of sulfuryl chloride was dropwise added and reacted at 45° C. for 1 h. The reaction mixture was then concentrated, 200 mL of N,N-dimethylformamide was added and heated to 130° C. until the reaction was complete. After that, the reaction mixture was cooled to room temperature, and extracted, washed, concentrated and separated to give 30.0 g of 2-(2,6-diethyl-4-methylphenyl) malononitrile (70% yield).

Example 7 Preparation of 2-(2,6-diethyl-4-methylphenyl) malononitrile

To a 250 mL three-necked flask equipped with a magnetic stirrer and a thermometer were sequentially added 125.0 g of chlorobenzene and 64.4 g of 2-(2,6-diethyl-4-methyl-2-ene-1-cyclohexylidene) malononitrile. The reaction mixture was stirred, heated to 50° C., 16.2 g of sodium methoxide was added. The reaction was stirred for 5 min. The reaction mixture was then cooled to 0° C., and introduced with chlorine gas until the reaction was complete. After that, the reaction mixture was concentrated, 300 mL of N-methylpyrrolidone was added and heated to 110° C. until the reaction was complete. The reaction mixture was cooled, extracted, washed, concentrated and separated to give 49.0 g of 2-(2,6-diethyl-4-methylphenyl) malononitrile (77% yield).

Example 8 Preparation of 2-(2,6-diethyl-4-methylphenyl) malononitrile

To a 500 mL three-necked flask equipped with a magnetic stirrer, a thermometer and a reflux condenser were sequentially added 125.0 g of chlorobenzene and 53.5 g of 2-(2,6-diethyl-4-methyl-2-ene-1-cyclohexylidene) malononitrile. The reaction mixture was stirred, heated to 50° C., 13.4 g of sodium methoxide added. The reaction was stirred for 5 min. The reaction mixture was cooled to 0° C., and introduced with chlorine gas until the reaction was complete. Subsequently, the reaction mixture was desolventized, 200 g of N,N-dimethylformamide and 0.85 g of LiCl were sequentially added and refluxed until the reaction was completed. After that, the reaction mixture was concentrated, washed and separated to give 47.2 g of 2-(2,6-diethyl-4-methylphenyl) malononitrile (89% yield).

Example 9 Preparation of 2-(2,6-diethyl-4-methylphenyl) malononitrile

To a 500 mL three-necked flask equipped with a magnetic stirrer, a thermometer and a reflux condenser were sequentially added 125.0 g of chlorobenzene and 53.5 g of 2-(2,6-diethyl-4-methyl-2-ene-1-cyclohexylidene) malononitrile. The reaction mixture was stirred, heated to 50° C., 13.4 g of sodium methoxide was added. The reaction was stirred for 5 min. The reaction mixture was cooled to 0° C., and introduced with chlorine gas until the reaction was complete. Subsequently, the reaction mixture was desolventized, 200 g of N,N-dimethylformamide and 1.17 g of NaCl were sequentially added and refluxed until the reaction was completed. The reaction mixture was concentrated, washed and separated to give 45.6 g of 2-(2,6-diethyl-4-methylphenyl) malononitrile (86% yield).

Example 10 Preparation of 2-(2,6-diethyl-4-methylphenyl) malononitrile

To a 250 mL three-necked flask equipped with a magnetic stirrer and a thermometer were sequentially added 85.0 g of tetrahydrofuran and 42.9 g of 2-(2,6-diethyl-4-methyl-2-ene-1-cyclohexylidene) malononitrile. The reaction mixture was stirred, heated to 50° C., 8.0 g of sodium hydroxide was added. The reaction was stirred for 5 min. After being cooled to room temperature, the reaction mixture was added with 32.7 g of a 5% sodium hypochlorite solution, adjusted to pH 3-4 with 10% hydrochloric acid, reacted at room temperature under stirring for 30 min and added with ethyl acetate for extraction. The organic phase was collected, washed, dried and concentrated, and then 200 mL of N,N-dimethylformamide was added. The reaction mixture was refluxed until the reaction was complete, and cooled, acidificated, washed, concentrated and separated to give 29.5 g of 2-(2,6-diethyl-4-methylphenyl) malononitrile (70% yield).

Example 11 Preparation of methyl 2-cyano-2-(2,6-diethyl-4-methylphenyl) acetate To a 250 mL three-necked flask equipped with a magnetic stirrer, a thermometer and a reflux condenser were sequentially added 60.0 g of ethyl acetate and 30.0 g of methyl 2-cyano-2-(2,6-diethyl-4-methyl-2-ene-1-cyclohexylidene) acetate. The reaction mixture was stirred, heated to 50° C., 6.8 g of sodium methoxide was added. The reaction was stirred for 5 min. The reaction mixture was cooled to 5° C., and was introduced with chlorine gas until the reaction was complete. The reaction mixture was then desolventized, 100 mL of N,N-dimethylformamide and 0.22 g of LiCl were sequentially added and refluxed until the reaction was complete. After that, the reaction mixture was concentrated, washed and separated to give 23.1 g of methyl 2-cyano-2-(2,6-diethyl-4-methylphenyl) acetate (81% yield).

$^1$H NMR (CDCl$_3$, 500 MHz, TMS): δ 6.95 (s, 2H), 3.80 (s, 3H), 2.76-2.59 (m, 4H), 2.32 (s, 3H), 1.24 (t, J=9.5 Hz, 6H).

$^{13}$C NMR (CDCl$_3$, 125 MHz): δ 166.5, 142.8, 139.2, 128.2, 123.9, 115.9, 53.7, 36.8, 26.3, 21.1, 15.0.

Example 12 Preparation of 2-(2,6-diethyl-4-methylphenyl) malonamide

To a 100 mL three-necked flask equipped with a magnetic stirrer and a thermometer were sequentially added 3.6 g of water and 50.0 g of concentrated sulfuric acid. The reaction mixture was stirred, heated to 45° C., 21.2 g of 2-(2,6-diethyl-4-methylphenyl) malononitrile was slowly added. The reaction was stirred for 5 h at 50° C. Then the reaction mixture was cooled, poured into ice water, and extracted with ethyl acetate. The organic phases were combined, dried and concentrated to give 24.1 g of 2-(2,6-diethyl-4-methylphenyl) malonamide (97% yield).

Example 13 Synthesis of Pinoxaden

To a 250 mL three-necked flask equipped with a magnetic stirrer, a thermometer and a reflux condenser were sequentially added 24.8 g of 2-(2,6-diethyl-4-methylphenyl) malonamide prepared in Example 12, 21.0 g of [1,4,5]-oxydiazepine dihydrochloride, 125.0 g of chlorobenzene and 40.4 g of triethylamine. The reaction mixture was refluxed for reaction. After the reaction was completed, the reaction mixture was cooled to room temperature, and 21.6 g of pivaloyl chloride was slowly added and reacted at room temperature under stirring for 2 h. The reaction mixture was then adjusted to pH 3-4 with diluted hydrochloric acid, and extracted with ethyl acetate. The organic phases were combined, dried, concentrated and crystallized with hexane to give 29.6 g of Pinoxaden (74% yield).

$^1$H NMR (CDCl$_3$, 500 MHz, TMS): δ 8.88 (s, 2H), 4.28-4.26 (m, 2H), 3.94-3.93 (m, 2H), 3.89-3.83 (m, 4H), 2.56-2.47 (m, 2H), 2.45-2.40 (m, 2H), 2.39 (s, 3H), 1.12 (t, J=9.0 Hz, 3H), 1.23 (s, 9H).

What is claimed is:

1. A method for preparing a 2-arylmalonic acid derivative of formula (3), comprising:
   (1) subjecting a compound (1) to an isomerization reaction in the presence of a base to obtain an intermediate (2), as shown in the following reaction scheme:

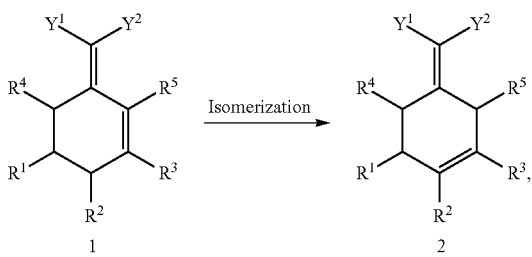

wherein the base is selected from the group consisting of an alkali metal hydroxide, an alkali metal alcoholate and a combination thereof; and (2) subjecting the intermediate (2) to a halogenation reaction in the presence of a halogenating agent to produce a halogenated product, and subjecting the halogenated product to a dehydrohalogenation-aromatization reaction under a temperature of 110-150° C. to obtain the 2-arylmalonic acid derivative (3), as shown in the following reaction scheme:

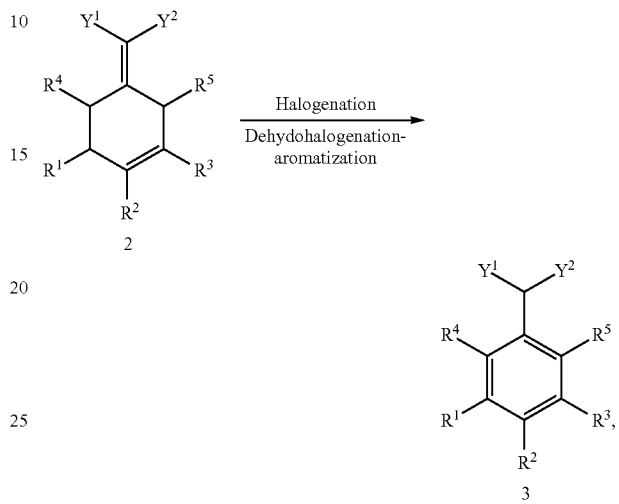

wherein the halogenating agent is selected from the group consisting of an elemental halogen and sulfuryl chloride;

wherein R$^1$, R$^2$, R$^3$, R$^4$ and R$^5$ are each independently hydrogen or a C$_1$-C$_4$ alkyl group;

Y$^1$ and Y$^2$ are each independently cyano, —COOMe or —COOEt.

2. The method of claim 1, wherein in step (1), a molar ratio of the base to the compound (1) is (0.8-2.4):1; and
   in step (2), the dehydrohalogenation-aromatization reaction is carried out under an action of a catalyst; the catalyst is an alkali metal halide; a molar ratio of the catalyst to the intermediate (2) is (0.005-2.4):1.

3. The method of claim 2, wherein in step (1), the base is sodium hydroxide or sodium methoxide; the molar ratio of the base to the compound (1) is (1.0-1.2):1; and
   in step (2), the molar ratio of the catalyst to the intermediate (2) is (0.02-0.1):1.

4. The method of claim 1, wherein the method is carried out in a one-pot manner.

* * * * *